United States Patent [19]

Bartoli et al.

[11] 4,126,033

[45] Nov. 21, 1978

[54] DETERMINATION OF THERMAL CONDUCTANCES OF BONDING LAYERS IN INFRARED PHOTOCONDUCTOR ARRAYS

[75] Inventors: Filbert J. Bartoli, Upper Marlboro, Md.; Leon Esterowitz, Springfield; Roger E. Allen, Alexandria, both of Va.; Melvin R. Kruer, Oxon Hill, Md.

[73] Assignee: The United States of America as represented by the Secretary of the Navy, Washington, D.C.

[21] Appl. No.: 809,490

[22] Filed: Jun. 23, 1977

[51] Int. Cl.² .......................................... G01N 25/18
[52] U.S. Cl. .................................................. 73/15 A
[58] Field of Search .............. 73/15 R, 15 A, 190 E, 73/190 W, 190 H; 324/65 R, 71 S, 71 N

[56] References Cited

U.S. PATENT DOCUMENTS

| | | | |
|---|---|---|---|
| 2,330,599 | 9/1943 | Koehni | 73/15 |
| 3,279,239 | 10/1966 | Arends et al. | 73/15 |
| 3,434,332 | 3/1969 | Maley | 73/15 |
| 3,566,669 | 3/1971 | Lawrence et al. | 73/15 |

FOREIGN PATENT DOCUMENTS 855,658  12/1960  United Kingdom ....................... 73/15

OTHER PUBLICATIONS

Bartoli et al., "Thermal Recovery Processes in Laser Irradiated HyCdTe(Pc) Detectors" in Applied Optics vol. 14 #10 Oct. 75 pp. 2499–2506.

*Primary Examiner*—Herbert Goldstein
*Attorney, Agent, or Firm*—R. S. Sciascia; Philip Schneider; Melvin L. Crane

[57] ABSTRACT

A method for determining in situ the thermal conductances of bonding layers of detectors in infrared detector arrays for quality selection of preferred detector arrays. Each detector of the array is heated successively by laser pulses of variable pulse width and the thermally-induced change in detector resistance is measured as a function of time after each laser pulse and converted directly to its corresponding temperature. Using measured values of detector resistance as a function of temperature for each detector, one can obtain the time-dependence of the detector temperature following each laser pulse for each detector of the array.

1 Claim, 2 Drawing Figures

DETERMINATION OF THERMAL CONDUCTANCES OF BONDING LAYERS IN INFRARED PHOTOCONDUCTOR ARRAYS

BACKGROUND OF THE INVENTION

This invention relates to infrared photoconductor arrays and more particularly to a method of assembly-line quality selection of thermally optimized photoconductive arrays.

It is well recognized that, during miliary use of electro-optical systems, the electro-optical elements may be irradiated by high-power laser beams. Thus, it is desirable to develop systems which will function in such an environment. In developing such systems, it is necessary that electro-optic arrays be checked to determine whether or not their operation is within required ranges.

It has been determined that a primary limitation of photoconductor array performance under high thermal loading is the inefficient thermal coupling between the heat-absorbing detector elements and the heat sink. In present state-of-the-art IR photoconductor arrays, the individual detectors in the array are bonded to a substrate by use of epoxy and the substrate is usually mounted on a cyrogenic heat sink by means of an adhesive layer such as a low-temperature varnish. The two bonding layers are thermally resistive and act as bottlenecks limiting the flow of heat from the detector elements to the heat sink.

In the fabrication of such IR detector arrays, wide variations in the thermal conductance between the detector element and the heat sink are observed due to imperfections in the bonding layers. It is necessary therefore to provide a technique for quality control and selection whereby the thermal conductances of the bonding layers may be measured in situ for each detector of an array as well as for each of the arrays of the assembly line.

Present techniques for measuring the thermal characteristics are restricted to DC bias-current effects. The main limitation to this approach is that it provides the thermal conductance of each detector in the array, but not of the individual layers comprising each detector of the array. Such a test provides information on steady-state power dissipation for a given detector but not on the thermal response of the detector to pulsed radiation.

Heretofore a method has been set forth in U.S. Pat. No. 4,012,691 for independently determining the thermal conductances of the two bonding layers of single-element detectors. In that technique the detector signal is measured during and after a laser pulse and is found to fall abruptly upon removal of the incident laser radiation; however, the signal does not completely return to its dark bias level until the resistance of the heated detector returns to its initial value. The recovery times are characteristic of heat transfer through the various layers of material. The magnitude of the thermally induced signal, the relative importance of the recovery processes and the exact shape of the thermal curve vary greatly with power density and irradiation time. Temperature profiles calculated for a laser-irradiated detector show that the bonding layers used to mount the IR detector on the substrate and the substrate on the heat sink are the two major factors limiting the performance of infrared photodetectors under high thermal loading.

Comparison of experimental thermal recovery curves with theoretical curves calculated by using a one-demensional thermal model allows one to determine the thermal properties of these two bonding layers. The above technique is successful for single IR detectors; however, the technique is not applicable for detector array assemblies. In single IR detectors, heat flow is essentially one-demensional, that is, heat flows in one direction from the IR detector material, through the epoxy bonding layer to the substrate and through the varnish layer to the heat sink. For detector arrays, heat flows not only in the direction from the detector material to the heat sink, but also perpendicular to that direction within the substrate. Because of this perpendicular component of heat flow, the technique set forth in U.S. Pat. No. 4,012,691 is not applicable to detector arrays and a more sophisticated approach to this thermal problem is required. Differences in the two systems have been set forth in a publication, "Thermal Conductance of Bonding Layers in Hgcdte (PC) Detector Arrays," by F. Bartoli et al., *Applied Optics* Vol. 15, No. 9 pp. 2016–2017, September 1976, which is incorporated herein by reference.

SUMMARY OF THE INVENTION

This invention is an optical technique for determining the thermal properties of bonding layers in operating IR photoconductive arrays to determine their quality of manufacture. Theoretical thermal recovery curves of an ideal detector array are calculated for each detector in the array. During the calculation, each detector of the array is divided into a large number of finite elements and the temperature of each detector is evaluated repeatedly by use of a heat-balance equation for each element using small time increments. After the detector has been heated by a laser pulse of the required intensity and duration, the incident laser flux is set to zero, and the temperature is calculated as the detector cools. The calculation is continued until the detector recovers to its initial temperature. This is repeated for each detector of the array so as to obtain a family of thermal profiles for each detector of the entire array. The family of thermal profiles represent curves of acceptable detectors in an array.

Thermal-recovery curves for each detector of an array to be tested for quality are obtained by successively heating each of the different detectors by laser pulses of different pulse width or for different time lengths and measuring the resistance of each detector after the laser pulse until the detector has cooled to its initial temperature. The resistance values obtained are changed directly into their corresponding temperature values or the device may be calibrated to read the resistance directly as temperature. By comparing the corresponding theoretically calculated and experimentally obtained thermal-recovery curves, the quality of the thermal properties of the two bonding layers associated with each detector of the tested array can be obtained.

DETAILED DESCRIPTION

Figure 1:
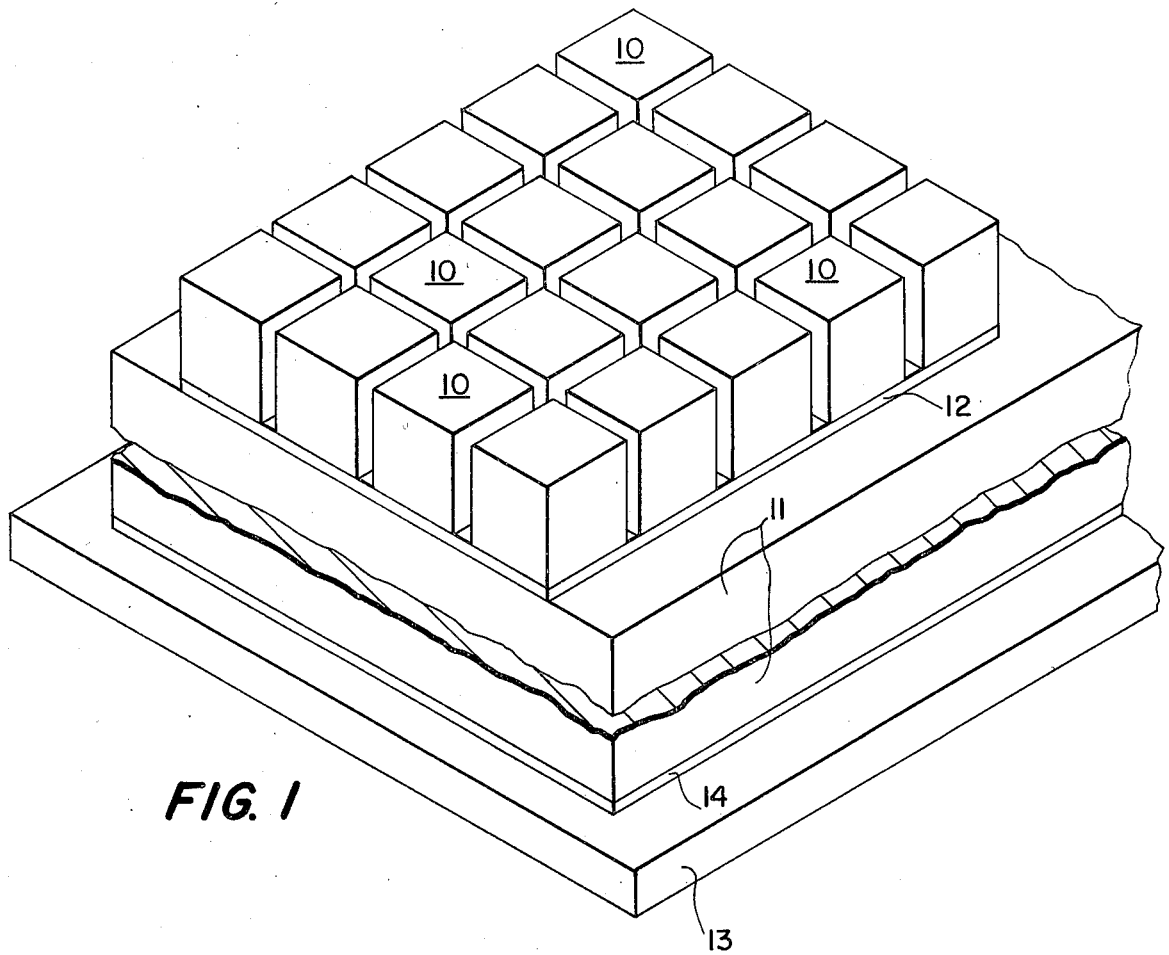
FIG. 1 is a perspective view of an array with the IR detectors spaced from each other.

Infrared detectors 10 such as a HgCdTe detector, for example, are shown evenly dispersed on a substrate 11 and secured in place by an epoxy 12 to form an array. The HgCdTe detectors and epoxy layers are typically from 5-20 μm thick, and 1-15 μm respectively. The substrate is secured to a heat sink 13 made from copper, for example, by any suitable low-temperature bonding means such as a GE7031 varnish 14. The substrate is typically from 250-1000 μm thick and the varnish is from 1-25 μm thick. Each detector element has two electrically conductive wires 15, 16 connected to opposite top edges which are connected with an electrical output-measuring device, 17 such as an oscilloscope not shown for simplification of the drawing. The measured output of each detector indicates the thermally induced change in detector resistance due to incident heat such as that resulting from a laser pulse 18 from laser element 19. The thermally induced change in detector resistance is measured and directly recorded in terms of its corresponding temperature as a function of time after the laser pulse. The measuring device may be calibrated directly to show temperature instead of resistance. The recorded curve for each detector represents details of the thermal recovery for each element which are sensitive to the values of thermal conductance for the epoxy and bonding layers.

Throughout the specification detector refers to one detector and array refers to all detectors on the substrate.

The ability of the detectors to dissipate heat is limited by the thermally resistant adhesive layers that bond the detector to the substrate and the substrate to the heat sink. As the detectors are irradiated by a heat source, the detectors heat-up, from which heat is conducted through the first bonding layer to the substrate and from the substrate through the second bonding layer to the heat sink. The first bonding layer creates a heat barrier which delays dissipation of heat to the substrate, then the second bonding layer creates a heat barrier which delays the dissipation of heat from the substrate to the heat sink. The amount of heat dissipated and time required for heat dissipation depends upon several different factors: the energy of the heat source, the length of time of heat application, the thickness of the bonding layers, the thermal properties of the material and the boundary conditions of the bonding layers. In order to select detector arrays of best quality, it is necessary to completely characterize the thermal properties of the array. Since the detectors change resistance due to heat and the resistance change is a function of the temperature of the detectors, the temperature of the detectors can be determined by measuring the resistance of the detector. Since it is difficult to measure the dissipation of heat when the detectors are being irradiated, the measurement may be made after the application of heat has ended. Thus, the thermal properties of the bonding layers are determined by measuring the resistance of the detectors after the laser pulse until the detector reaches its initial temperature and by converting the resistance values directly into temperature. These experimental thermal profiles are then compared to theoretical profiles. As set forth earlier, this measurement is not a direct vertical heat flow measurement since the heat travels horizontally as well as vertically.

In carrying out the teaching of this invention, thermal-recovery measurements for each IR detector of a detector array are compared with theoretical calculations obtained using a numerical thermal model. In obtaining the calculated curves for a numerical thermal model, each detector of an IR detector array is divided into a large number of finite elements and a heat-balance equation is evaluated repeatedly for each finite element using small time increments. The heat-balance equation contains terms representing absorption of laser energy and heat flow into and out of each finite element. One arbitrary detector of the detector array is heated by a laser pulse of the required intensity and duration and the incident laser flux is then set to zero. The temperature is calculated by monitoring the resistance change due to cooling until the detector recovers to its initial temperature. This is repeated for all detectors of the array. Thus, thermal-recovery curves for each detector in the array may be calculated.

This approach allows one to treat sample inhomogeneities, composite layered structures and time dependent irradiation conditions. The rate $Q_{Z_{i,j,k}}$ at which heat flows in the Z direction from element $(i,j,k)$ into element $(i,j,k+1)$ is given approximately by the product of the thermal conductance and the temperature difference $(T_{i,j,k}+T_{i,j,k+1})$ between the centers of the two elements. If both elements have the same thermal conductivity, the thermal conductance is given simply by the product of the thermal conductivity K and the area of the interface $A_{Z_{i,j,k}}$ divided by the distance between the centers of the elements. Generally, the thermal conductivities of adjacent elements ($K_{i,j,k}$ and $K_{i,j,k+1}$) are not the same and the thermal conductance between the centers of two adjacent elements is:

$$A_{Z_{i,j,k}} \left[ \frac{\Delta Z_k}{2K_{i,j,k}} + \frac{\Delta Z_{k+1}}{2K_{i,j,k+1}} \right]^{-1}$$

Therefore $Q_{Z_{i,j,k}}$ is given by $$Q_{Z_{i,j,k}} = (T_{i,j,k} - T_{i,j,k+1}) A_{Z_{ijk}} \left[ \frac{\Delta Z_k}{2K_{i,j,k}} + \frac{\Delta Z_{k+1}}{2K_{i,j,k+1}} \right]^{-1}$$

Similar expressions describe heat flow in the X and Y directions.

Heat can also enter the element by absorption from extermal sources (e.g., optical radiation). An additional term, $P_{i,j,k}$ (watts), represents the rate at which heat is added externally to the $(i,j,k)$ element. The net rate of energy flow into the $(i,j,k)$ element is determined by adding the heat flux entering the element and subtracting the flux leaving, using the equation:

$$\Delta Q_{i,j,k} = P_{i,j,k} + Q_{X_{i-1,j,k}} - Q_{X_{i,j,k}} + Q_{Y_{i,j-1,k}} - Q_{Y_{i,j,k}} + Q_{Z_{i,j,k-1}} - Q_{Z_{i,j,k}}.$$

For the $i,j,k$ element, the temperature increase $\Delta T_{i,j,k}$ during the time increment, $\Delta t$, is $$\Delta T_{i,j,k} = \frac{\Delta Q_{i,j,k} \Delta t}{C_{i,j,k} M_{i,j,k}}$$

where $C_{i,j,k}$ and $M_{i,j,k}$ are the specific heat and mass respectively of the $(i,j,k)$ element. The heat balance is performed repeatedly using a small time increment $\Delta t$ until the sum of the time increments equals the time of interest. At each time step, the temperature change $\Delta T_{i,j,k}$ is added to the previous temperature $T_{i,j,k}$. The temperature after an irradiation time $\tau = n\Delta t$ (i.e., $n$ time intervals) is $$T_{i,j,k} = T_{ref} + \sum_{q=1}^{n} \Delta T_{i,j,k} \quad (q)$$

where $\Delta T_{i,j,k}(q)$ is the temperature change calculated for the $q$'th time interval.

Figure 2:
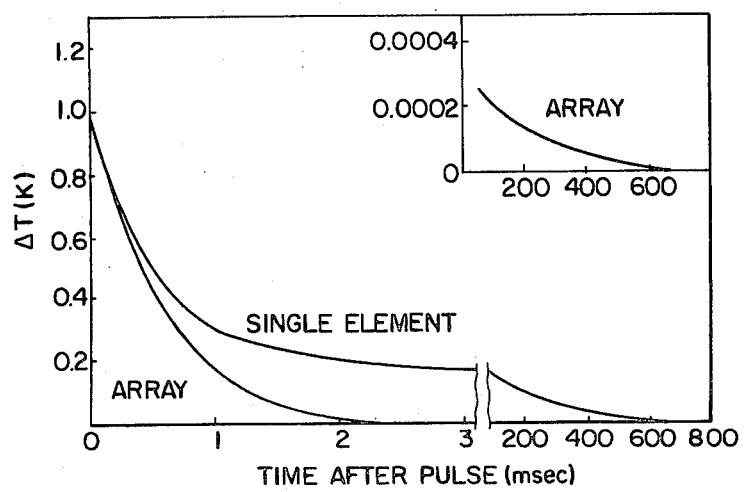
FIG. 2 illustrates the thermal recovery curve for one HgCdTe detector of a photoconductive array compared with that of a single detector. The inset shows on an expanded temperature scale the long time recovery for the array element.

FIG. 2 compares a calculated thermal recovery curve for one detector of an IR detector array with that of a single element IR detector. The temperature decrease subsequent to laser heating is plotted as a function of time after the laser pulse. The inset shows, on an expanded temperature scale, the long-time recovery for the array element. The short time recovery (on the order of milliseconds) is very sensitive to the thermal properties of the epoxy layer but independent of those of the varnish layer. This part of the thermal recovery is therefore used to determine the thermal conductance of the epoxy bonding layer. The long time recovery, shown in the inset of FIG. 2 (on the order of hundreds of milliseconds, is sensitive to the thermal properties of the varnish bonding layer but not those of the epoxy. Therefore this part of the thermal recovery is used to determine the thermal conductance of the varnish layer. The calculations for the curves shown in FIG. 2 were determined by exposing each detector of a 12 detector array to a 200$\mu$ sec. $CO_2$ laser pulse of 16.5 W/cm$^2$. Each detector measured 200 $\mu$m on a side and the thickness of the different parts of the assembly were the same.

A model can be made for different laser intensities and different incident time durations to cover various parameters of interest. Once the models have been formulated, the thermal-recovery curves for each detector of an operating IR photoconductive array can be compared with those calculated by the models and a least-squares fit can be obtained, thereby determining the values of thermal conductances of the bonding layers for each detector of interest from the values obtained in the fit.

In carrying out the method, each detector of a "laser-hardened" IR photoconductor array is heated successively by laser pulses of variable pulse width and the thermally induced change in detector resistance is measured and directly recorded in terms of their corresponding temperature as a function of time after each laser pulse. Thermal recovery for each detector of the array is sensitive to the values of thermal conductance for the epoxy and varnish bonding layers associated with each particular detector of the array. Using measured values of resistance as a function of temperature for each detector of the array, a predetermined model allows one to calculate the recovery of the detector following each laser pulse for each detector of the array. Using the thermal conductances of the bonding layers are adjustable parameters, the values of the thermal conductances are determined independently for each detector by fitting the recovery data to the theoretical curves.

The method of this invention makes possible an accurate determination in situ of the thermal conductances of the bonding layers for each detector in a detector array. It can be used to evaluate performance and characterize uniformity of a photoconductive array under thermal loading, as well as to compare the power-handling capability of different arrays. These capabilities can be determined for pulsed as well as continuous wave laser irradiation.

This method may be used for quick assembly-line quality selection of thermally optimized photoconductive arrays. This can be carried out in many ways by use of a properly programmed on-line computer. For example, the numerical-thermal-model information may be stored in the computer and like information for an unknown array fed into the computer where the computer searches for a match. In this way the thermal conductances of the bonding layers are determined for each detector of the tested array. If these values do not meet predetermined minimum requirements stored in the computer, the array will be rejected. Thus, it is seen that fast quality testing of IR photoconductive detector arrays may be checked with minimum effort by an operator.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A method of determining in-site the thermal conductances of bonding layers of IR detectors in a test array of infrared detectors which comprises:
   simultaneously scanning all detectors of said array with a laser beam having a specific intensity such that said laser beam dwells on each detector of said array for a set time duration;
   setting the incident laser beam intensity to zero;
   recording the temperature of each of said detectors and the time at said zero intensity setting;
   continuously recording the time and temperature change of each of said detectors from said zero setting until the initial preheated temperature is reached to obtain a thermal recovery curve of each of said detectors;
   comparing the recorded thermal recovery curve for each of said detectors with a calculated family of thermal recovery curves using like laser intensities and beam duration and thermal conductances of different bonding layers employed in fabricating said detectors of said array thereby obtaining from said comparison individual thermal conductances of each of said bonding layers of said array of detectors;
   repeating said heat-record steps for other laser beam intensities and time durations of incidence to obtain a family of thermal recovery curves for each of said detectors at different laser beam intensities and time durations;
   comparing the measured and calculated thermal recovery curves for each of said laser beam intensities and laser beam durations to determining the optimum laser intensity and beam duration for determining the thermal conductance of a first bonding layer of each of said detectors;
   said optimum laser beam intensity and pulse duration being different for each of said detectors;
   repeating said latter comparison step for determining the thermal conductance of a second bonding layer of each of said detectors;
   whereby the thermal conductances of said first and second bonding layers are derived from said optimum laser intensities and pulse durations obtained separately for each of said layers.

* * * * *